United States Patent
Bergman et al.

(10) Patent No.: US 10,779,775 B2
(45) Date of Patent: Sep. 22, 2020

(54) X-RAY MARKER GUIDED AUTOMATED GUIDE WIRE OR WORKING CATHETER ADVANCEMENT

(71) Applicant: Corindus, Inc., Waltham, MA (US)

(72) Inventors: Per Bergman, West Roxbury, MA (US); Steven Blacker, Framingham, MA (US); Robert Elden, Cambridge, MA (US); Jerry Jennings, Chelsea, MA (US); Nicholas Kottenstette, Worcester, MA (US); Jean-Pierre Schott, Weston, MA (US)

(73) Assignee: CORINDUS, INC., Waltham, MA (US)

( * ) Notice: Subject to any disclaimer, the term of this patent is extended or adjusted under 35 U.S.C. 154(b) by 0 days.

(21) Appl. No.: 13/964,388

(22) Filed: Aug. 12, 2013

(65) Prior Publication Data
US 2015/0005620 A1     Jan. 1, 2015

Related U.S. Application Data (60) Provisional application No. 61/839,459, filed on Jun. 26, 2013.

(51) Int. Cl.
*A61B 5/00*     (2006.01)
*A61B 6/12*     (2006.01)
(Continued)

(52) U.S. Cl.
CPC .............. *A61B 6/12* (2013.01); *A61B 6/485* (2013.01); *A61B 6/487* (2013.01); *A61B 6/504* (2013.01);
(Continued)

(58) Field of Classification Search
CPC ...................................................... A61B 5/00
(Continued)

(56) References Cited

U.S. PATENT DOCUMENTS 5,334,294 A * 8/1994 Iwai .................... B23H 9/18
                                                     205/664
5,395,353 A    3/1995 Scribner
(Continued)

FOREIGN PATENT DOCUMENTS

| EP | 1421913 | 5/2004 |
|---|---|---|
| EP | 2322088 | 5/2011 |

OTHER PUBLICATIONS

Ginapp, Todd; Ask the Clinical Instructor (A Q&A for those new to the cath lab); pp. 38-39; Cath Lab Digest; vol. 16-Issue 8; Aug. 2008; URL https://www.cathlabdigest.com/articles/Ask-Clinical-Instructor-11; 2 pages.

*Primary Examiner* — Joel F Brutus
(74) *Attorney, Agent, or Firm* — Rathe Lindenbaum LLP (57) ABSTRACT

Disclosed is the automated rapid advancement of a guide wire through a guide catheter using x-ray markers. The procedure involves providing a guide wire with a marker at or adjacent its tip, providing a guide catheter with a marker at or adjacent its distal terminus, rapidly advancing the guide wire through the guide catheter from its proximal end to its distal end under the control of an automated apparatus, and terminating the automated rapid advancement when the guide wire tip marker becomes adjacent to the guide catheter distal end marker. Fluoroscopic images may be taken of the of the guide wire as it rapidly advances through the guide catheter and image processing software used to determine when to terminate the rapid advancement. This software may use either the position or the velocity of the guide wire to make this determination.

10 Claims, 5 Drawing Sheets

(51) Int. Cl.
*A61M 25/09* (2006.01)
*A61B 6/00* (2006.01)
*A61B 34/20* (2016.01)
*A61M 25/01* (2006.01)
*A61F 2/958* (2013.01)
*A61M 25/10* (2013.01)
*A61B 17/22* (2006.01)
*A61B 17/00* (2006.01)
*A61B 18/00* (2006.01)
*A61B 34/30* (2016.01)
*A61B 90/00* (2016.01)
*A61B 34/10* (2016.01)

(52) U.S. Cl.
CPC .............. *A61B 34/20* (2016.02); *A61F 2/958* (2013.01); *A61M 25/0113* (2013.01); *A61M 25/09041* (2013.01); *A61M 25/104* (2013.01); *A61B 2017/00075* (2013.01); *A61B 2017/22042* (2013.01); *A61B 2018/00375* (2013.01); *A61B 2018/00386* (2013.01); *A61B 2034/107* (2016.02); *A61B 2034/2065* (2016.02); *A61B 2034/301* (2016.02); *A61B 2090/061* (2016.02); *A61B 2090/376* (2016.02); *A61B 2090/3966* (2016.02); *A61M 25/0108* (2013.01); *A61M 2025/0166* (2013.01); *A61M 2025/09166* (2013.01)

(58) Field of Classification Search
USPC ........................................................ 600/424
See application file for complete search history.

(56) References Cited

U.S. PATENT DOCUMENTS

| | | | |
|---|---|---|---|
| 5,851,172 A * | 12/1998 | Bueche | A61N 5/1007 600/3 |
| 6,587,709 B2 | 7/2003 | Solf et al. | |
| 7,033,325 B1 | 4/2006 | Sullivan | |
| 7,403,811 B2 | 7/2008 | Sathanarayana | |
| 7,599,730 B2 | 10/2009 | Hunter et al. | |
| 7,697,972 B2 | 4/2010 | Verard et al. | |
| 7,769,427 B2 | 8/2010 | Shachar | |
| 7,873,402 B2 | 1/2011 | Shachar | |
| 7,887,549 B2 | 2/2011 | Wenderow et al. | |
| 2003/0097062 A1 | 5/2003 | Toth et al. | |
| 2003/0144590 A1 | 7/2003 | Maschke | |
| 2004/0097805 A1 | 5/2004 | Verard et al. | |
| 2004/0102697 A1 | 5/2004 | Evron | |
| 2004/0106916 A1 | 6/2004 | Quaid et al. | |
| 2005/0065434 A1 | 3/2005 | Bavaro et al. | |
| 2005/0256398 A1 | 11/2005 | Hastings et al. | |
| 2006/0015126 A1* | 1/2006 | Sher | 606/159 |
| 2006/0241465 A1 | 10/2006 | Huennekens et al. | |
| 2006/0247521 A1 | 11/2006 | McGee | |
| 2007/0073271 A1* | 3/2007 | Brucker et al. | 604/537 |
| 2007/0135709 A1 | 6/2007 | Rioux et al. | |
| 2008/0097187 A1 | 4/2008 | Gielen et al. | |
| 2008/0097195 A1 | 4/2008 | Urquhart et al. | |
| 2008/0123922 A1 | 5/2008 | Gielen et al. | |
| 2008/0262473 A1* | 10/2008 | Kornblau et al. | 604/529 |
| 2009/0001276 A1* | 1/2009 | Yagi et al. | 250/370.09 |
| 2009/0207965 A1 | 8/2009 | Sakaguchi | |
| 2009/0281418 A1 | 11/2009 | Ruijters et al. | |
| 2011/0137156 A1 | 6/2011 | Razzaque et al. | |
| 2011/0251483 A1 | 10/2011 | Razzaque et al. | |
| 2011/0319752 A1 | 12/2011 | Steinberg et al. | |
| 2012/0071751 A1 | 3/2012 | Sra et al. | |
| 2012/0071752 A1* | 3/2012 | Sewell et al. | 600/424 |
| 2012/0071782 A1* | 3/2012 | Patil et al. | 600/547 |
| 2012/0136242 A1 | 5/2012 | Qi et al. | |
| 2014/0187920 A1 | 7/2014 | Millett et al. | |
| 2015/0005620 A1 | 1/2015 | Bergman et al. | |
| 2015/0005738 A1 | 1/2015 | Blacker | |
| 2015/0005745 A1 | 1/2015 | Bergman et al. | |
| 2015/0005865 A1 | 1/2015 | Bergman et al. | |
| 2015/0164445 A1 | 6/2015 | Blau et al. | |

* cited by examiner

X-RAY MARKER GUIDED AUTOMATED GUIDE WIRE OR WORKING CATHETER ADVANCEMENT

CROSS-REFERENCE TO RELATED PATENT APPLICATIONS

This application is a Non-Provisional of U.S. Provisional Application No. 61/839,459, filed Jun. 26, 2013, entitled "ROBOTIC IMAGE CONTROL SYSTEM", of which is incorporated herein by reference in its entirety.

BACKGROUND OF THE INVENTION

Systems exist for the robotic feeding of percutaneous interventional devices such as guide wires and working catheters into guide catheters. The guide catheters are typically placed by manual manipulation of medical personnel such that their distal ends are adjacent to the site of action for the intervention, typically a valve or chamber of the heart or a lesion in a blood vessel such as an artery. In the case of coronary arteries the guide catheter may be placed adjacent to the entrance of the artery into the aorta. The interventional devices such as guide wires and working catheters may be fed by the operation of robotic controls by medical personnel such as shown in U.S. Pat. No. 7,887,549. The working catheters may be equipped with balloons, stents or stents enclosing balloons.

SUMMARY OF THE INVENTION

The present invention involves the automated rapid advancement of a guide wire through a guide catheter using x-ray markers. The procedure involves providing a guide wire with a marker at or adjacent its tip, providing a guide catheter with a marker at or adjacent its distal terminus, rapidly advancing the guide wire through the guide catheter from its proximal end to its distal end under the control of an automated apparatus, and terminating the automated rapid advancement when the guide wire tip marker becomes adjacent to the guide catheter distal end marker.

BRIEF DESCRIPTION OF THE DRAWINGS

This application will become more fully understood from the following detailed description, taken in conjunction with the accompanying figures, wherein like reference numerals refer to like elements in which:

FIG. 4 (a) and FIG. 4 (b) are schematics of various configurations of X-ray markers on a guide catheter.

DETAILED DESCRIPTION OF THE PREFERRED EMBODIMENTS

Figure 1:
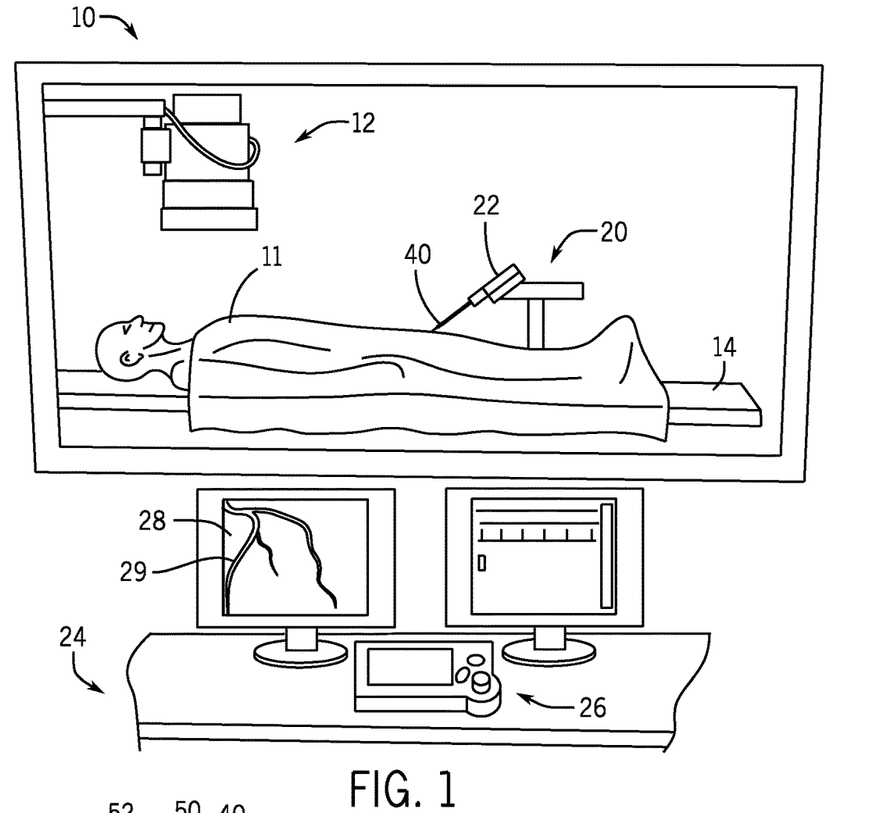
FIG. 1 is a schematic of the environment in which percutaneous interventional procedures are robotically performed.

Referring to FIG. 1, the environment in which the various embodiments of the present invention find particular utility involves a catheter laboratory 10 for robotically performing percutaneous interventional procedures. A patient 11 is supported on a table 14 and the procedure is observed with fluoroscopic X-ray equipment 12. A cassette 22 supported by a robotic arm 20 which is used to automatically feed a guide wire 50 (shown in FIG. 2) into a guide catheter 40 seated in an artery 60 (shown in FIG. 5) of the patient 11. The cassette 22 is controlled from a remote station 24 in order to isolate the medical personnel conducting the procedure from exposure to the X-ray radiation used to monitor the procedure by use of fluoroscopic equipment. The station includes remote controls 26 for controlling the cassette 22 and a screen 28 with which to monitor the progress of the procedure. It displays the arterial system 29 being addressed by the procedure. U.S. Pat. No. 7,887,549, incorporated herein by reference, has a detailed disclosure of this environment.

Figure 2:
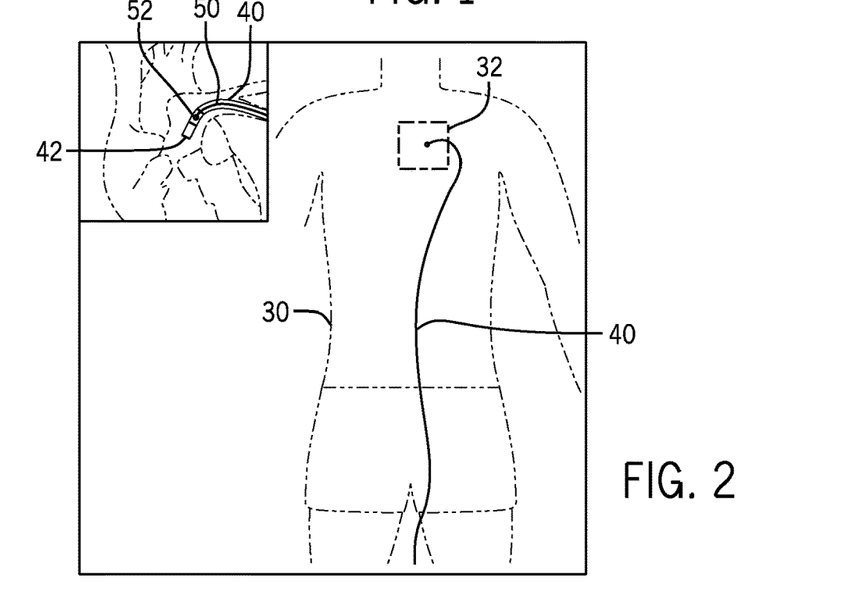
FIG. 2 is a schematic of the placement of a guide catheter and a guide wire in a human body.

Referring to FIG. 2, a guide catheter 40 that has been fed into the torso 30 of a patient 11 to reach the cardiac region 32. Within the guide catheter 40 is a guide wire 50 whose tip 52 has not yet passed out of the distal end 42 of the guide catheter 40. The X-ray equipment which is used to monitor the progress of the guide wire 50 as it passes through the guide catheter 40 and approaches its distal terminus 42 may be controlled such that it images the entire path until the guide wire tip enters the cardiac region 32 and then just images the cardiac region 32. It may also be controlled to take images at a more frequent rate once the tip 52 enters the region 32.

Figures 3, 4:
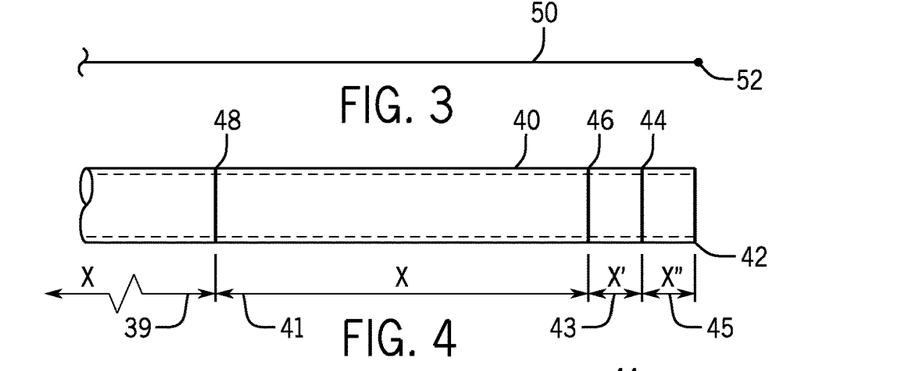
FIG. 3 is a schematic of a guide wire carrying an X-ray marker.
FIG. 4 is a schematic of a guide catheter carrying X-ray markers.

Referring to FIG. 3, a guide wire 50 terminates at its distal end with a tip 52 that contains an X-ray marker that is readily apparent in a fluoroscopic image of the tip 52.

Referring to FIG. 4, a guide catheter 40 with a distal terminus 42 has been provided with a distal X-ray marker 44, an intermediate X-ray marker 46 and a proximate X-ray marker 48. It has a length 39 which extends from its proximal end to the intermediate X-ray marker 48 as well as a length 41 from there to the intermediate X-ray marker 46, a length 43 from that X-ray marker to the distal X-ray marker 44 and a length 45 from the distal X-ray marker 44 to its distal end 42. These markers 44, 46 and 48 and theses lengths 39, 41, 43 and 45 may be used to control the movement of a guide wire or working catheter being fed through the guide catheter 40. For instance, image-processing software may be used to analyze iteratively successive fluoroscopic images of the distal portion of the guide catheter and recognize when the X-ray marker in the guide wire tip 52 has first passed the markers 48, 46 and 44. This information can then be used to control the movement and speed of a guide wire 50 being fed to the guide catheter via its proximal end. In one embodiment the guide wire 50 can be quickly fed until its tip 52 until it reaches the marker 48 when the feed speed can be reduced and then the automatic feed can be terminated when the tip 52 reaches the marker 46. In another approach, when the tip 52 reaches the marker 46 the feed speed is reduced and then the feed is terminated when the tip 52 reaches the marker 44. This two stage feeding procedure provides automatic feeding that ceases closer to the distal terminus 42 of the guide catheter 40 with reduced risk of overshooting the terminus 42. The distances 39, 41, 43 and 45 may be used to set feeding velocities appropriate for the rate of taking fluoroscopic images and the latency time of the image processing software. Alternatively, these distances may be used to calculate the effective feeding velocity of the guide wire 50 and determine an appropriate time to terminate the automatic feeding such that the tip 52 does not emerge from the distal terminus 42.

Figure 4A:
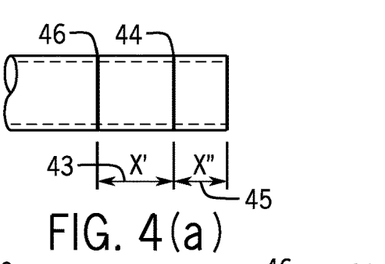

Referring to FIG. 4 (a), an alternative uses just two markers 46 and 44. In this case the distance 43 is greater than distance 45. This supports an approach in which the feed is slowed when marker 46 is reached and stopped when marker 44 is reached.

Figure 4B:
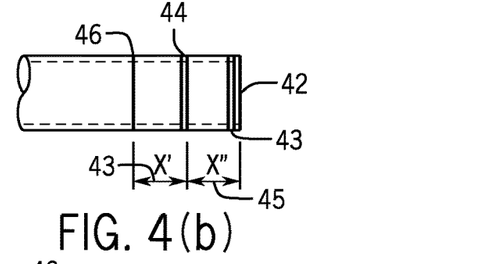

Referring to FIG. 4 (b) an alternative uses an X-ray marker 43 immediately adjacent to the terminus 42 and each of the markers 43, 44 and 46 has been given a distinctive character so that the image processing software is aided in distinguishing them.

Referring to FIG. 5A-H, X-ray markers and image processing software control an interventional procedure from feeding a guide wire 50 to a guide catheter 40 to the secure placement of an angioplasty balloon 80 across a lesion 62 in an artery 60.

Figure 5A:
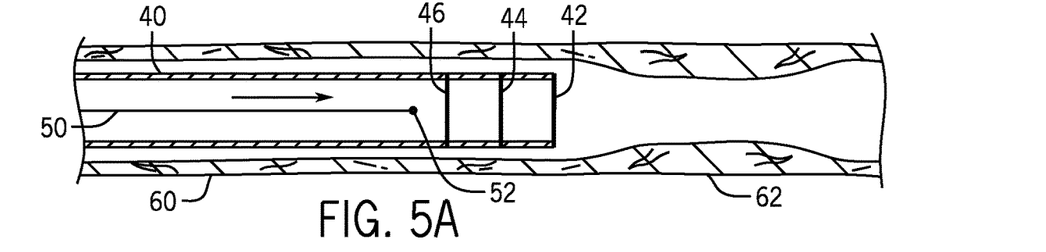
FIG. 5A-5H are schematics of a procedure of placing an angioplasty balloon over a lesion using a guide catheter, a guide wire, a working catheter and X-ray markers.

Referring to FIG. 5A, the guide wire 50 is being fed at an accelerated rate into a guide catheter 40 which is seated in an artery 60 with, for ease of illustration, its distal end adjacent to a lesion 62. In the case of coronary arteries, there may be a considerable distance between this distal end and the lesion, as the common practice is to have this distal end at the ostium of the artery down which the guide wire is to be fed. The lesion may be a considerable distance downstream from this point and may be in an artery which branches off this artery. The tip 52 has yet to cross the intermediate marker 46.

Figure 5B:
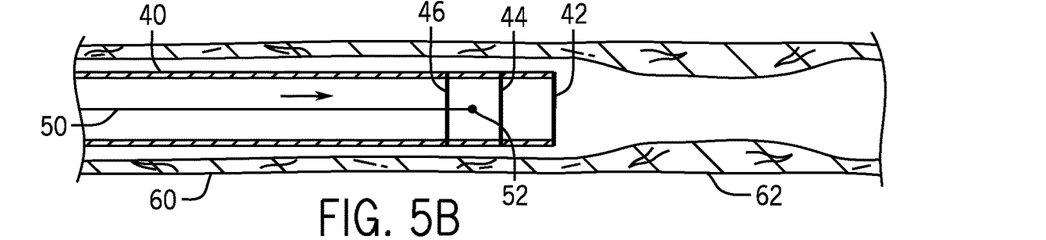

Referring to FIG. 5B, the tip 52 has been detected as having passed the intermediate marker 46 by the image processing software, which is analyzing iterative fluoroscopic images of the progress of the guide wire 50, and this software has caused a decrease in the feed velocity.

Figure 5C:
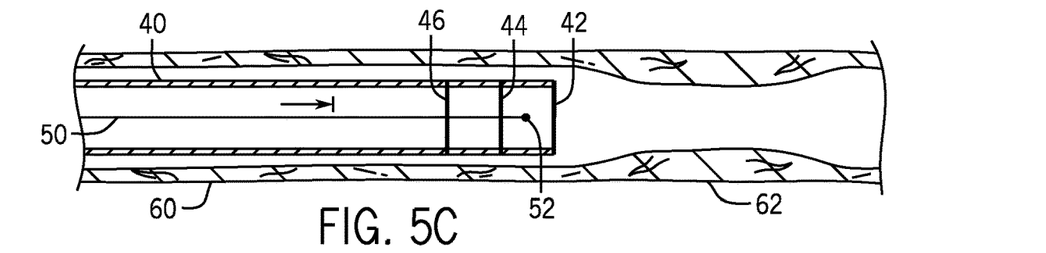

Referring to FIG. 5C, the image processing software has detected that the tip 52 has passed the distal X-ray marker 44 and has further slowed or stopped the feeding of the guide wire. In the latter case, a signal has been sent indicating to the medical personnel conducting the procedure that manual advancement of the guide wire is needed.

Figure 5D:
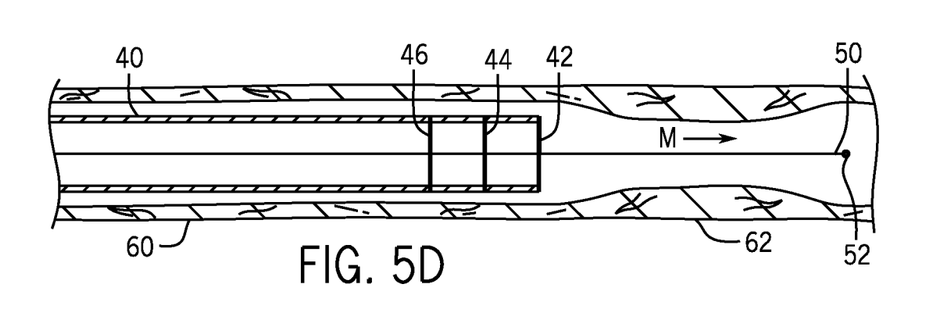

Referring to FIG. 5D, the tip 52 has been advanced out of the distal terminus 42 of the guide catheter 40 and across the lesion 62. This could have been done manually or by image processing software that recognizes the lesion 62. In the case of coronary arteries or other situations in which there is a considerable distance from the distal end 42 of the guide catheter 40 to the lesion 62, the guide wire may be advanced this distance by a human operator using the remote controls 26.

Figure 5E:
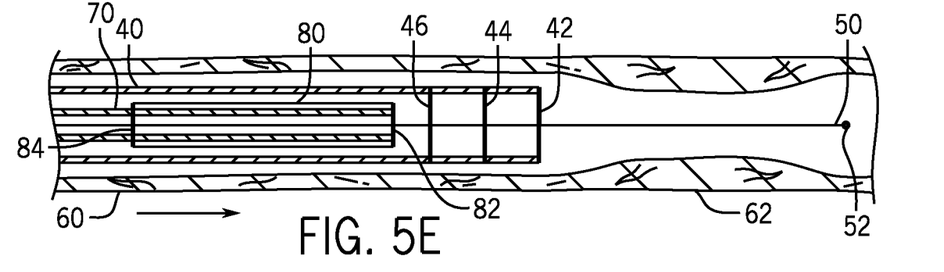

Referring to FIG. 5E, a working catheter 70 carrying an angioplasty balloon 80 at its distal end has been advanced over the guide wire 50 but has not yet reached the X-ray marker 46. The balloon 80 carries X-ray markers at both its distal end 82 and its proximal end 84.

Figure 5F:
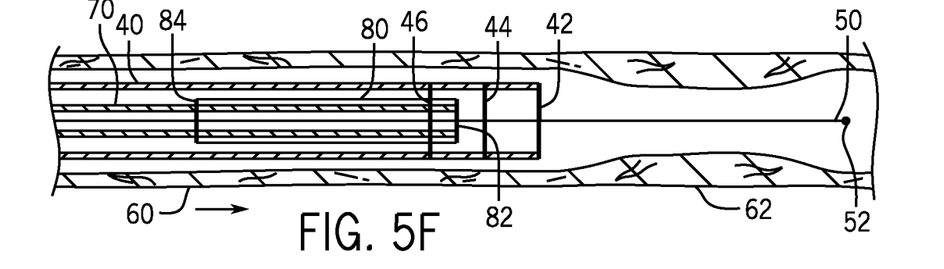

Referring to FIG. 5F, the distal end 82 of the balloon 80 has passed marker 46 and thus the image processing software has slowed the feed rate of the working catheter 70.

Figure 5G:
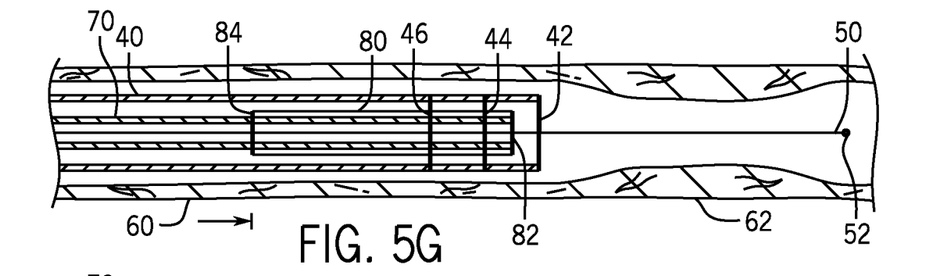

Referring to FIG. 5G, the end 82 has passed marker 44. The image processing software has either signaled to the medical personnel conducting the procedure that manual advancement of the working catheter 70 is needed or it has slowed the advancement rate. Because the path of travel has been established by the guide wire 50, this advancement may be automated and under control of the image processing software even if there is a considerable distance to the lesion such as may be the case with a coronary artery.

Figure 5H:
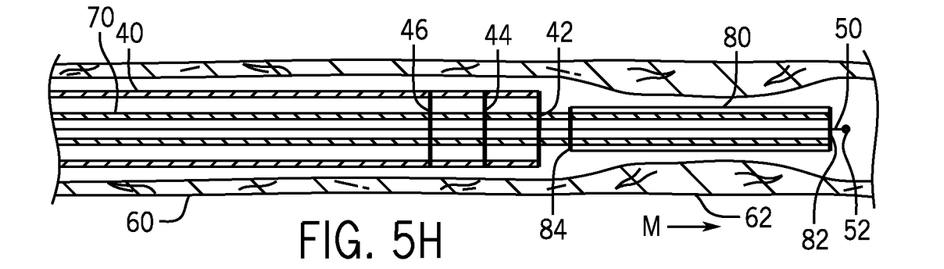

Referring to FIG. 5H, the balloon has been advanced across the lesion 62 either manually or under control of image processing software that can recognize the lesion 62. The balloon may carry a stent for deployment across the lesion.

Figure 6:
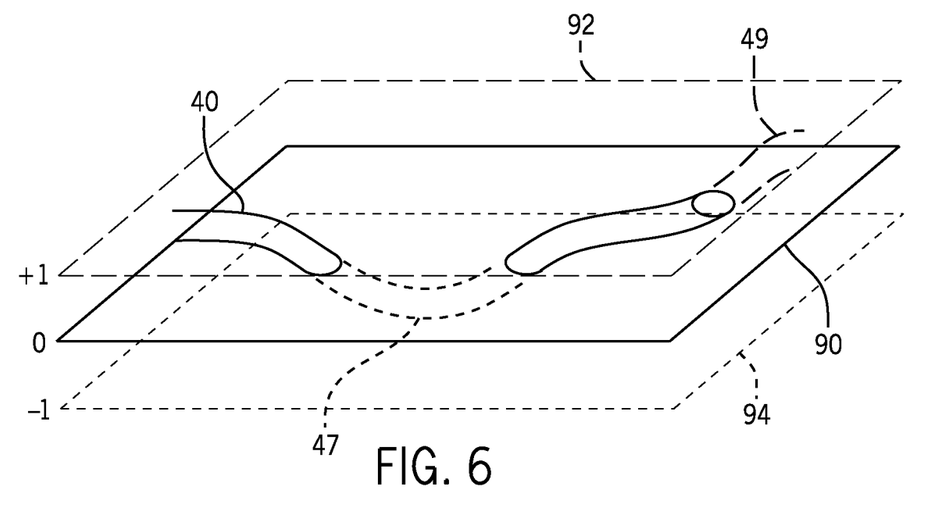
FIG. 6 is a schematic of a guide catheter in relationship to the plane of a 2-D fluoroscopic image.

Referring to FIG. 6, a guide catheter 40 follows the path of an artery that is not illustrated. It has a portion 47 that has passed below the plane 90 of the fluoroscopic image into a lower plane 94 and it has a portion 49 that has passed above the plane 90 into a higher plane 92. Iterative fluoroscopic images in plane 90 can be combined with measurements of the length of guide wire being fed into the guide catheter to yield an indication of the 3-D path of the guide catheter and therefore the artery itself.

Figure 7:
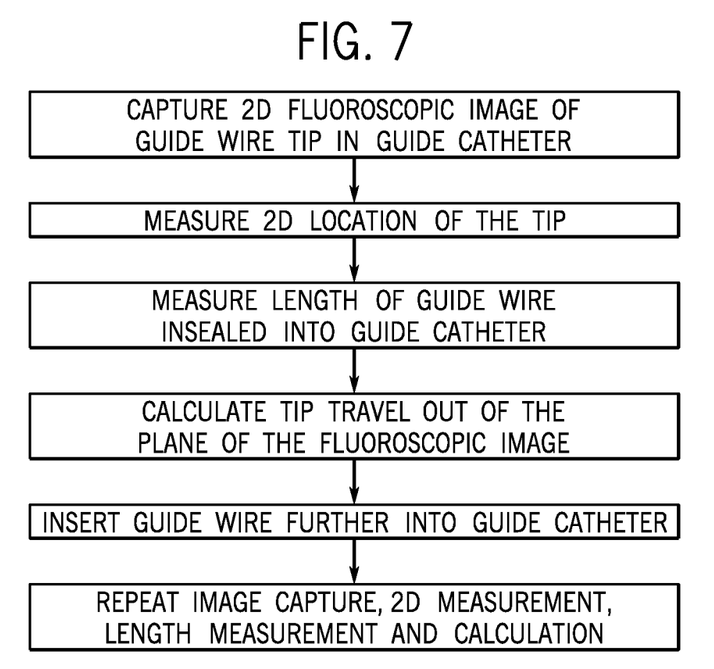
FIG. 7 is a flow diagram of creating a 3-D map of the path of a guide wire being fed into a guide catheter.

Referring to FIG. 7, a step-by-step procedure may be followed to develop the indication of the 3-D path from iterative fluoroscopic images.

Figure 8:
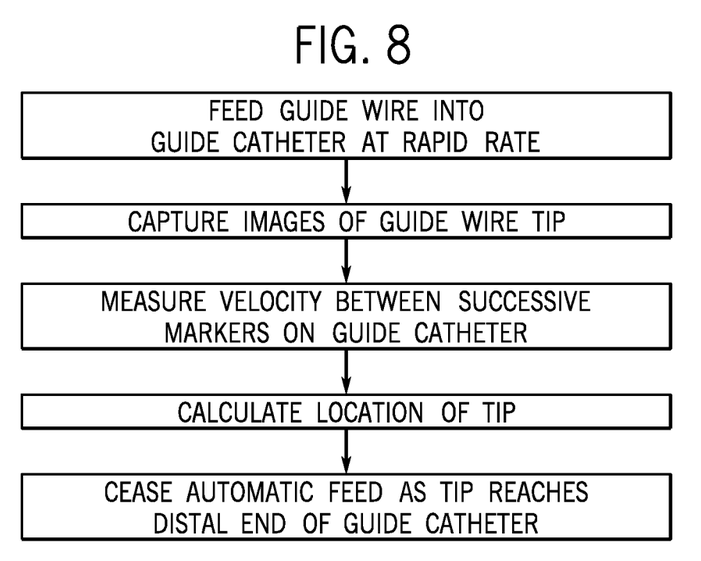
FIG. 8 is a flow diagram of the automated feeding of a guide wire into a guide catheter.

Referring to FIG. 8, a procedure for controlling the feeding of a guide wire 50 to a guide catheter 40 such that it does not emerge from the distal terminus 42 of the guide catheter may use velocity measurements.

Figure 9:
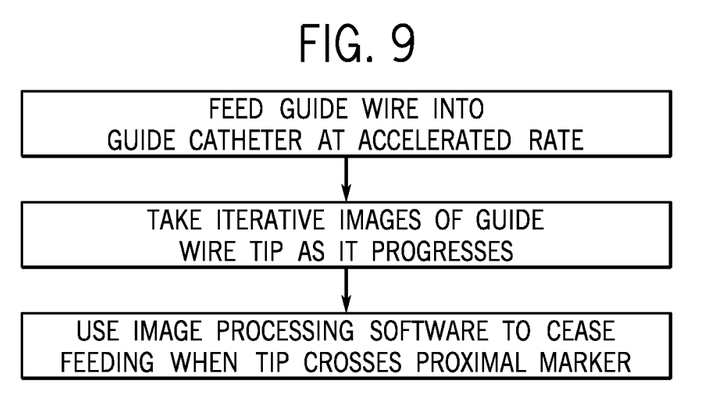
FIG. 9 is a flow diagram of the automated feeding of a guide wire into a guide catheter.

Referring to FIG. 9, a procedure for controlling the feeding of a guide wire 50 to a guide catheter 40 such that it does not emerge from the distal terminus 42 of the guide catheter may use iterative fluoroscopic images.

An embodiment involves automatically advancing a guide wire or working catheter (i.e. a catheter that carries a balloon, a stent or both) through a guide catheter until it is close to the end of the guide catheter adjacent to the site of action such as a blood vessel lesion or a chamber or valve of the heart. In the case of a coronary artery, the distal end of the guide catheter may be disposed in the aorta with the distal end of its lumen coaxial with the opening of the coronary artery down which the guide wire or working catheter is to be passed. The tip of the guide wire or the distal end of the working catheter and the distal end of the guide catheter may both be provided with an X-ray marker visible in a fluoroscopic image.

An embodiment involves providing additional markers, possibly distinctive, to better monitor the progress of the guide wire or working catheter in the guide catheter. The additional markers may be on the guide catheter or the guide wire or working catheter being fed or both. Fluoroscopic images in which these markers appear may be combined with information about the length of guide wire or working catheter fed into the guide catheter to estimate the position of the tip of the guide wire or the end of the working catheter. The multiple markers on the guide catheter may also be used to estimate the effective velocity of the guide wire or working catheter as it is being fed through the guide catheter and this effective velocity may take account of the travel out of the plane of the fluoroscopic images.

The control mechanism of the drive feeding the guide wire or working catheter into the guide catheter causes the feeding to substantially slow or stop as the two markers approach each other. One approach involves taking fluoroscopic images of the progress of the guide wire or working catheter through the guide catheter and using image processing software to estimate the distance between the two markers. The feeding can then be slowed or stopped when the distance falls below a preset value. The X-ray exposure of the patient may be reduced by taking intermittent fluoroscopic images and the frame rate may be selected in accordance with the velocity of feeding of the guide wire or working catheter.

When multiple markers are used on either the guide wire or working catheter and the guide catheter, redundant detection of a set of markers decreases the risk of overshooting the end of the guide catheter by imposing a stop if a maker or a set of markers preceding the last distal marker are not detected within a predefined length of guide wire or working catheter.

The use of multiple markers increase the accuracy of the velocity estimation by averaging multiple measurements individually affected by variable foreshortening due to the out of fluoroscopic plane wire incursion.

Additionally, accuracy of the velocity and tip position is increased by the use of a precomputed 3D map of the arteries that take into account foreshortening.

An embodiment involves providing proximal markers for greater safety. One approach is to provide additional markers on the guide catheter spaced proximally from its distal end and using these markers to better assure the control of the emergence of the guide wire or working catheter out of the distal end of the guide catheter.

An embodiment involves determining the true length of a lesion in a blood vessel. The length of a lesion may be important in determining the appropriate therapeutic approach such as determining the appropriate length of a balloon or stent used to address the lesion. An X-ray marker on a guide wire is aligned with one end of a lesion and then moved until it is aligned with the other end of the lesion. The alignment is determined by fluoroscopic imaging. Then the difference in the length of guide wire inserted into the blood vessel between the two alignments is determined and is a measure of the true length of the lesion as opposed to just its projection into the plane of a fluoroscopic image. In one embodiment the first alignment is with the distal end of the lesion and the guide wire is withdrawn from the blood vessel to effect the second alignment. This approach should minimize any errors due to kinking of the guide wire.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A process for automatically advancing a guide wire through a guide catheter comprising:
    providing a guide wire with a marker at or adjacent its tip;
    providing a guide catheter with a proximate marker and a distal marker at or adjacent its distal terminus, wherein the proximate marker is further from the distal terminus than the distal marker;
    advancing the guide wire within the guide catheter with an automated apparatus;
    analyzing iteratively successive fluoroscopic images of a distal portion of the guide catheter and the marker on the guide wire;
    providing instructions to the automated apparatus to automatically reduce the speed of the advance of the guide wire when the tip of the guide wire reaches the proximate marker of the guide catheter; and
    terminating advancing of the guide wire when the guide wire tip marker reaches the guide catheter marker adjacent its distal terminus.

2. The process of claim 1 wherein:
    fluoroscopic images are taken of the guide wire as it advances through the guide catheter; and
    estimating a distance between the guide wire tip marker and the marker adjacent the distal terminus of the guide catheter; and
    providing instructions to the automated apparatus to slow the advance of the guide wire when an estimated distance becomes smaller than a preset value.

3. The process of claim 2 wherein:
    the fluoroscopic images are taken intermittently such that an image is taken when the estimated distance is at the preset value.

4. The process of claim 3 wherein providing instructions to the automated apparatus to slow the advance of the guide wire occurs when the estimated distance becomes smaller than a preset value; wherein the estimated distance is used to set a velocity of the guide wire for a rate of taking fluoroscopic images and the latency time of imaging processing.

5. The process of claim 1 wherein:
    the guide catheter is provided with multiple markers at known distances along its length;
    fluoroscopic images are taken of the guide wire as it advances through the guide catheter; and
    estimating a velocity of the guide wire during its advancement in the guide catheter.

6. The process of claim 5 wherein:
    the fluoroscopic images are taken at a frame rate which is adjusted in accordance with the estimated velocity;
    estimating a distance between guide wire tip marker and the guide catheter distal end marker; and
    terminating the automated advancing of the guide wire when the estimated distance becomes smaller than a preset value.

7. The process of claim 6 wherein the distal end of the guide catheter is immediately adjacent to the ostium of a coronary artery in the aorta.

8. The process of claim 1 further including taking x-ray images of an entire path of the guide catheter while the tip of the guide wire is within the guide catheter; and taking x-ray images of just the cardiac region once the tip of the guide wire exits the guide catheter.

9. The process of claim 8, wherein taking x-ray images occurs at a more frequent rate once the tip of the guide catheter exits the distal end of the guide catheter.

10. A process for automatically advancing a guide wire through a guide catheter comprising:
    providing a guide wire with a marker at or adjacent its tip;
    providing a guide catheter with a marker at or adjacent its distal terminus;
    advancing the guide wire within the guide catheter at a feed speed with an automated apparatus;
    analyzing iteratively successive fluoroscopic images of a distal portion of the guide catheter and the marker on the guide wire;
    providing instructions to the automated apparatus to automatically reduce the speed of the advance of the guide wire as the tip of the guide wire approaches the distal terminus of the guide catheter; and
    providing instructions to automatically terminate the advancement of the guide wire tip when the guide wire tip becomes adjacent to the guide catheter marker adjacent its distal terminus.

* * * * *